United States Patent [19]

Rosenthal

[11] Patent Number: 5,204,532
[45] Date of Patent: Apr. 20, 1993

[54] METHOD FOR PROVIDING GENERAL CALIBRATION FOR NEAR INFRARED INSTRUMENTS FOR MEASUREMENT OF BLOOD GLUCOSE

[75] Inventor: Robert D. Rosenthal, Gaithersburg, Md.

[73] Assignee: Futrex, Inc., Gaithersburg, Md.

[21] Appl. No.: 717,198

[22] Filed: Jun. 18, 1991

Related U.S. Application Data

[63] Continuation-in-part of Ser. No. 682,249, Apr. 9, 1991, Pat. No. 5,068,536, which is a continuation-in-part of Ser. No. 565,302, Aug. 10, 1990, Pat. No. 5,077,476, which is a continuation-in-part of Ser. No. 544,580, Jun. 27, 1990, Pat. No. 5,086,229, which is a continuation-in-part of Ser. No. 298,904, Jan. 19, 1989, Pat. No. 5,028,787.

[51] Int. Cl.$^5$ .............................................. G01N 21/59
[52] U.S. Cl. .................................. 250/341; 250/252.1; 128/633
[58] Field of Search ............ 250/341, 339, 343, 252.19; 128/633; 356/39

[56] References Cited

U.S. PATENT DOCUMENTS

| | | |
|---|---|---|
| 3,493,774 | 2/1970 | Knudsen . |
| 3,958,560 | 5/1976 | March . |
| 4,608,990 | 9/1986 | Elings .................................. 128/633 |
| 4,805,623 | 2/1989 | Jobsis .................................. 128/633 |
| 4,975,581 | 12/1990 | Robinson et al. .................... 250/343 |
| 5,068,536 | 11/1991 | Rosenthal ............................ 250/341 |
| 5,070,874 | 12/1991 | Barnes et al. ......................... 356/39 |

FOREIGN PATENT DOCUMENTS

| | | |
|---|---|---|
| 074428 | 3/1983 | European Pat. Off. . |
| 140633 | 5/1985 | European Pat. Off. . |
| 262779 | 4/1988 | European Pat. Off. . |
| 426358 | 5/1991 | European Pat. Off. . |
| 572309 | 2/1976 | Switzerland . |

OTHER PUBLICATIONS

Mueller et al., "Glucose Determination—State of the Art and Prospects", Biomedizinische Technik 25, 26–32 (1980).

Muller, "In Vivo Measurement of Glucose Concentration with Lasers", Hormone and Metabolic Record Supp. Series, vol. 8 1979, Stuttgart, DE Copy of European Search Report from EP 90 2878.

Primary Examiner—Paul M. Dzierzynski
Assistant Examiner—Richard Hanig
Attorney, Agent, or Firm—Rothwell, Figg, Ernst & Kurz

[57] ABSTRACT

A method is disclosed for accurately providing general calibration of near-infrared quantitative analysis instruments for almost any individual user. The general calibration method comprises comparing an individual's near-infrared spectrum to a plurality of near-infrared spectral clusters. Each near-infrared spectral cluster has a set of calibration constants associated therewith. The calibration constants of the spectral cluster most closely associated with the individual spectra are used to custom calibrate the near-infrared analysis measurement instrument.

4 Claims, 7 Drawing Sheets

METHOD FOR PROVIDING GENERAL CALIBRATION FOR NEAR INFRARED INSTRUMENTS FOR MEASUREMENT OF BLOOD GLUCOSE

CROSS-REFERENCE TO RELATED APPLICATION

This application is a continuation-in-part of copending application Ser. No. 07/682,249, now U.S. Pat. No. 5,068,536 filed Apr. 9, 1991, which is a continuation-in-part of copending application Ser. No. 07/565,302, now U.S. Pat. No. 5,077,476 filed Aug. 10, 1990, which is a continuation-in-part of copending application Ser. No. 07/544,580, now U.S. Pat. No. 5,086,229 filed Jun. 27, 1990, which is a continuation-in-part of copending application Ser. No. 07/298,904, now U.S. Pat. No. 5,028,787 filed Jan. 19, 1989.

BACKGROUND OF THE INVENTION

1. Field of the Invention

This invention relates to instruments and methods for the non-invasive quantitative measurement of blood analytes. More specifically, this invention relates to a method for providing general calibration for near-infrared instruments for measurement of blood analytes.

2. Description of Background Art

Information concerning the chemical composition of blood is widely used to assess the health characteristics of both people and animals. For example, analysis of the glucose content of blood provides an indication of the current status of metabolism. Blood analysis, by the detection of above or below normal levels of various substances, also provides a direct indication of the presence of certain types of diseases and dysfunctions.

A current type of blood glucose analytical instrumentation is available for the specific purpose of determining blood glucose levels in people with diabetes. This technology uses a small blood sample from a finger poke which is placed on a chemically treated carrier and is inserted into a portable battery operated instrument. The instrument analyzes the blood sample and provides a blood glucose level reading in a short period of time.

A different class of blood glucose analytical instruments is the near-infrared quantitative analysis instrument which noninvasively measures blood glucose, such as the type described in copending application Ser. No. 07/565,302. The noninvasive blood glucose measurement instrument analyzes near-infrared energy following interactance with venous or arterial blood, or transmission through a blood-containing body part. These instruments give accurate blood glucose level readings and readily lend themselves to at-home testing by diabetics.

A limitation of the near-infrared blood glucose measurement instruments has been that each instrument may be required to be custom calibrated for each individual user. The need for individual custom calibration results from the different combination of water level, fat level and protein level in various individuals which causes variations in energy absorption. Since the amount of glucose in the body is less than one thousandth of these other constituents, variations of these constituents which exist among different people has made a general or universal calibration appear unlikely.

The current approach for custom calibrating near-infrared blood glucose measurement instruments is to use an in-vitro technique that requires removing blood from the subject and having an automatic instrument measure the glucose level of that blood. Such in-vitro measurements are typically made with either the commercially available Biostator or the experimental Kowarski Continuous Monitor. Each of the above instruments requires a catheter to be inserted into the subject and blood withdrawn over a one to two hour period. Although such an approach is feasible, it places a significant new burden on the doctor and the medical facility to have enough time, room and equipment to be able to calibrate instruments in this fashion.

In another technique, a low-cost method and means is used for providing custom calibration for near-infrared instruments for measurement of blood glucose which comprises obtaining a plurality of blood samples from an individual at a predetermined time interval and for a predetermined period of time. Blood glucose measurements for each blood sample are obtained and are entered into the near-infrared instrument. Noninvasive near-infrared optical absorption measurements are concomitantly taken through a body part of the individual at a second predetermined time interval and are recorded in the analysis instrument. Calibration regression analysis is then performed utilizing means for linearly interpolating the blood sample glucose measurements with the near-infrared optical measurements to custom calibrate the near-infrared instrument for the individual. Although representing a significant advancement in custom calibration, this technique does not permit virtually any user to obtain accurate blood glucose level measurements without first having to individually calibrate the instrument. As a result, individual custom calibration can be a significant burden on time and on medical facilities.

Thus, there is a great need for a technique which allows an individual user to obtain fast and accurate blood glucose level measurements without having to first individually calibrate the analysis instrument.

SUMMARY OF THE INVENTION

In accordance with the present invention, a method of calibration is disclosed for calibrating a near-infrared instrument for the measurement of a blood analyte to accommodate almost any individual user. The calibration method according to the present invention comprises obtaining a near-infrared optical measurement from an individual and comparing the optical measurement with a plurality of spectral data clusters. Each spectral data cluster has associated therewith a set of calibration constants for calibrating the analysis instrument for the individual. The individual's optical measurement data is compared to the plurality of spectral data clusters to determine which cluster the data most closely identifies with. The calibration constants associated with that cluster are then used to calibrate the near-infrared analysis instrument for that individual. This calibration method is a significant advancement in near-infrared analysis instrument calibration because accurate calibration can be accomplished for any given individual without having to go through the custom calibration techniques of the prior art.

In another aspect of the present invention, a multiple calibration method is used to provide additional accuracy in blood analyte measurements. The multiple calibration method involves applying a near-infrared optical measurement to a first calibration which calibrates the optical measurement over substantially the entire range of possible blood analyte concentrations and produces a first calibrated value. Further, the first calibration determines whether the first calibrated value falls into a first higher range or a first lower range of possible blood analyte concentrations. A higher range calibration is selected for the first higher range and which calibrates the first calibrated value over the higher range. A lower range calibration is also selected for the first lower range and calibrates the first calibrated signal over the lower range. Based on which range the first calibrated value falls within, an appropriate second calibration is applied to provide a highly accurate measurement of blood analyte concentration.

DETAILED DESCRIPTION OF THE PREFERRED EMBODIMENTS

The present invention is directed toward a method for generally calibrating a noninvasive near-infrared blood glucose measurement instrument. An example of such a near-infrared blood glucose instrument is illustrated in copending application Ser. No. 07/565,302, incorporated herein by reference.

In conventional near-infrared analysis, the analysis instrument must be custom calibrated for each individual user. Individual custom calibration is a time consuming procedure often requiring invasive blood samples and resulting in a burden on health care facilities. Custom calibration for the individual user was generally thought to be required because different combinations of water level, fat level and protein level in various individuals cause variations in energy absorption.

Figure 1:
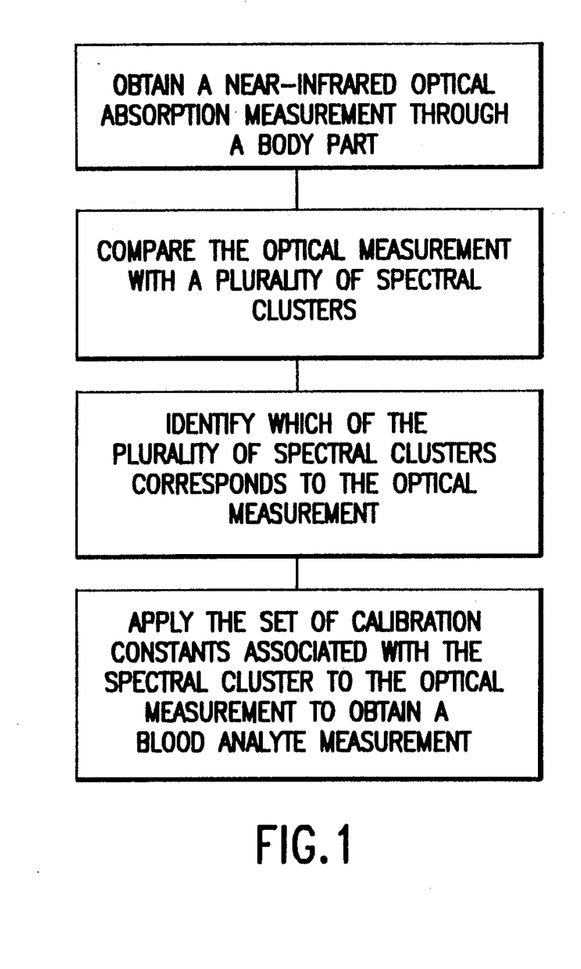
FIG. 1 is a flow diagram illustrating the method for calibrating a near-infrared analysis instrument for the measurement of blood glucose levels according to one embodiment of the present invention.

FIG. 1 illustrates a calibration method according to the present invention which alleviates the need to provide custom calibration for each individual user by utilizing a technique which automatically calibrates the analysis instrument for virtually any individual user. Thus, the general calibration method allows virtually any individual to obtain almost immediate, accurate blood analyte concentration measurements, without prior custom calibration.

The general calibration method according to the present invention is based upon a discovery that the shapes of the near-infrared spectral data distribution for all individuals, between about approximately 600 and approximately 1,000 nanometers, can be subdivided and categorized into a plurality of different "clusters" or "shapes." The concept of clusters is to subdivide a set of samples that have different characteristics into sets having similar characteristics. Cluster theory allows separating samples into distinct separate groups (i.e. clusters), thereby allowing each group to be identified by the type of constituent obtained. In blood glucose analysis, the spectral data distribution is subdivided into approximately six different clusters.

A set of calibration constants associated with each cluster is calculated and stored in the near-infrared analysis instrument.

General calibration for any individual user is accomplished by obtaining a near-infrared optical measurement spectrum, through a body part, and by comparing the optical measurement spectrum to each of the prestored spectral clusters. The general calibration method of the present invention utilizes means for identifying and assigning a particular cluster from among the six clusters that most closely matches the individual near-infrared optical measurements. Thus, any near-infrared spectra from any individual user can be assigned or matched to a specific cluster.

The calibration constants associated with the cluster identified as being most closely corresponding to the measured individual spectrum are then used to calibrate the analysis instrument. Accurate blood glucose level measurements are thereby obtained without having to custom calibrate the analysis for the individual user.

Figure 2A:
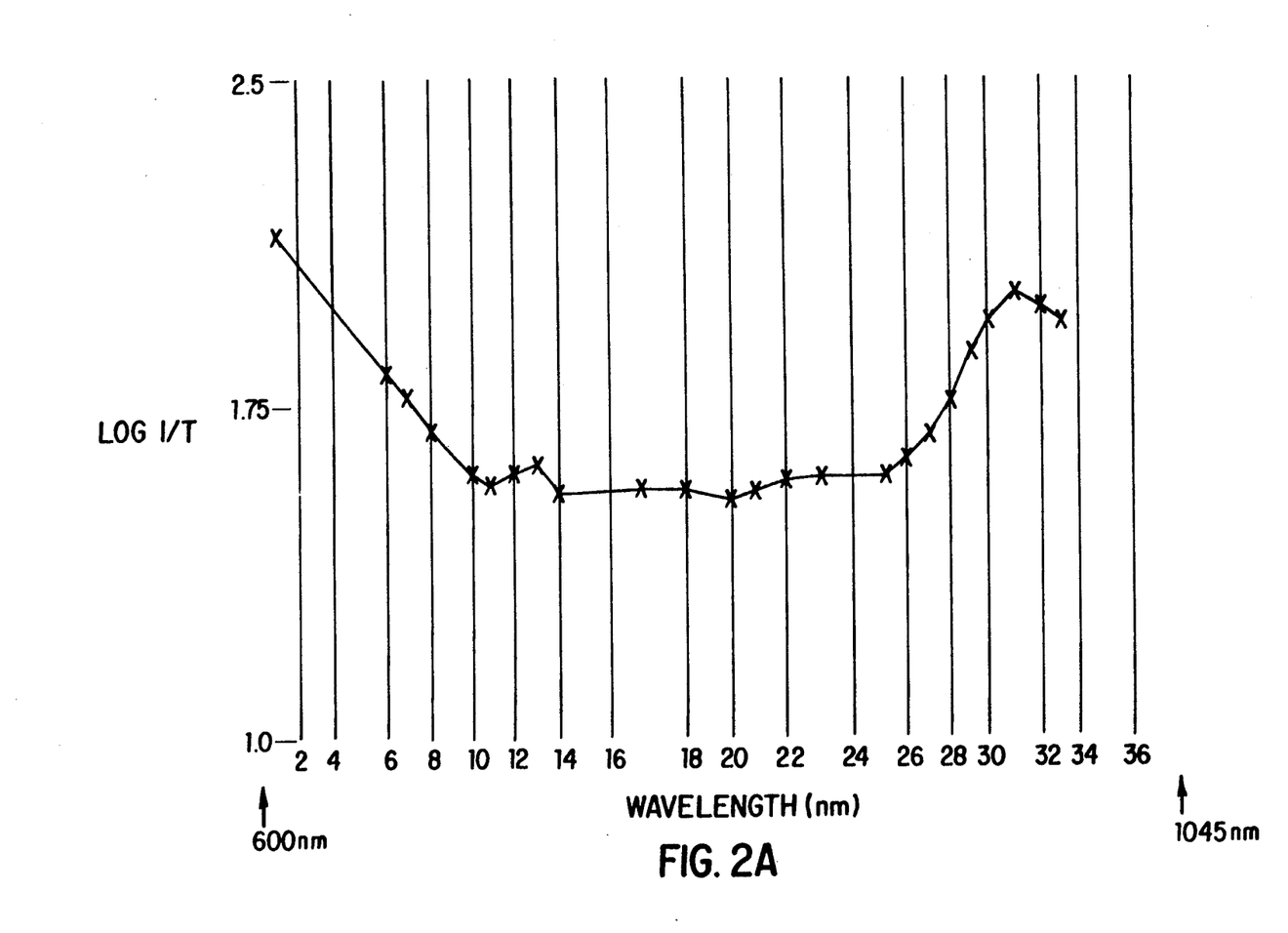
FIGS. 2A–C are graphs illustrating spectra clusters according to the present invention.
Figure 2B:
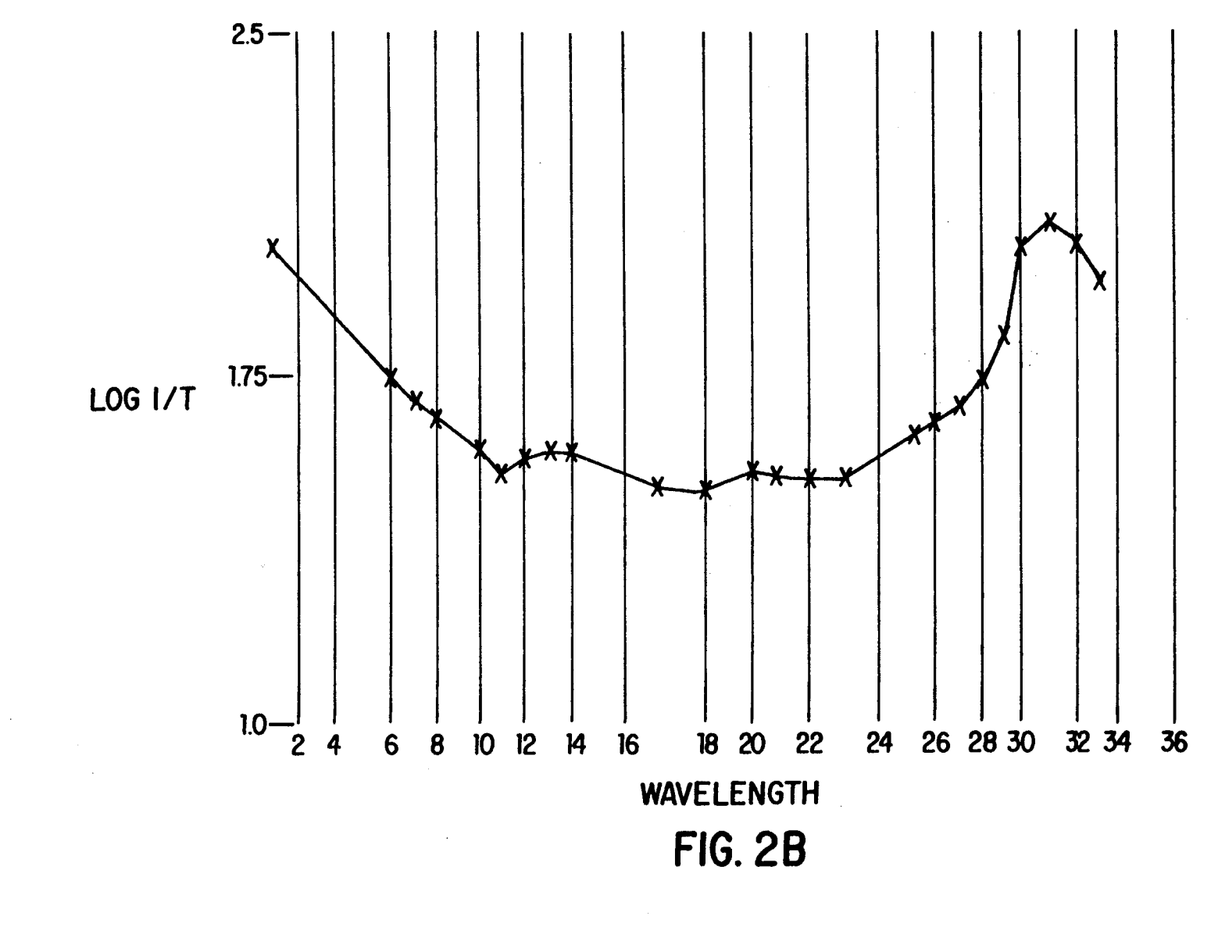
Figure 2C:
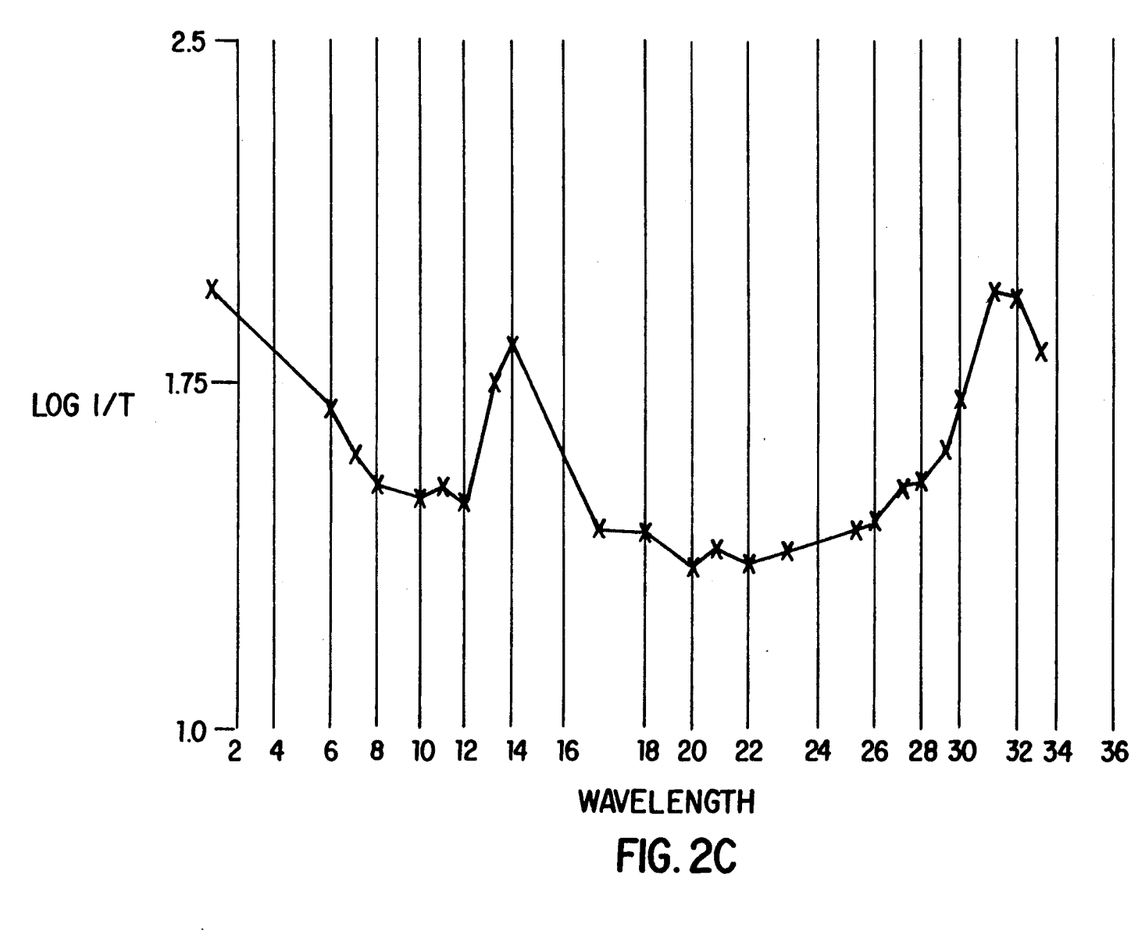

Grouping the individual samples into clusters can be accomplished in any suitable manner. In one approach, all sample spectral curves are visually observed, and representative curves that have certain significant differences from each other are identified and grouped into clusters. FIGS. 2A–C show curves which illustrate these clusters. As shown therein, the vertical axis is Log 1/T (optical density value), and the horizontal axis is wavelength which varies between 600 nanometers to 1000 nanometers. The vertical lines represent the specific optical filters that are installed in the analysis instrument to produce a desired wavelength. These Figures illustrate examples of clusters uniquely identified from large quantities of near-infrared spectral curve samples.

Once the clusters have been identified, assignment of the individual spectral data measurements thereto can be accomplished in any suitable way. In one embodiment, the optical measurement data is statistically compared with the cluster data. Specifically, this is done by calculating the square of the correlation coefficient ("$R^2$") between the measurement curve data, from the body part being measured, and the "master scan" or prestored distribution curve for each cluster. The cluster with the highest $R^2$ value to that individual measurement, i.e. typically a finger measurement, would be the appropriate cluster for application of calibration constants. A correlation of approximately 0.90 or higher results in accurate calibration. The blood glucose level for that individual would then be calculated using the calibration constants for that cluster.

Another method for identifying and assigning a particular near-infrared spectral cluster to the individual measured spectrum involves using general statistical analysis software, such as SAS ("Statistical Analysis Systems") made by SAS Instruments, Inc., Cary, N.C. The SAS analysis provides fast and accurate determination of the spectral clusters, and which cluster the individual's measured spectral data most closely fits.

Figure 3:
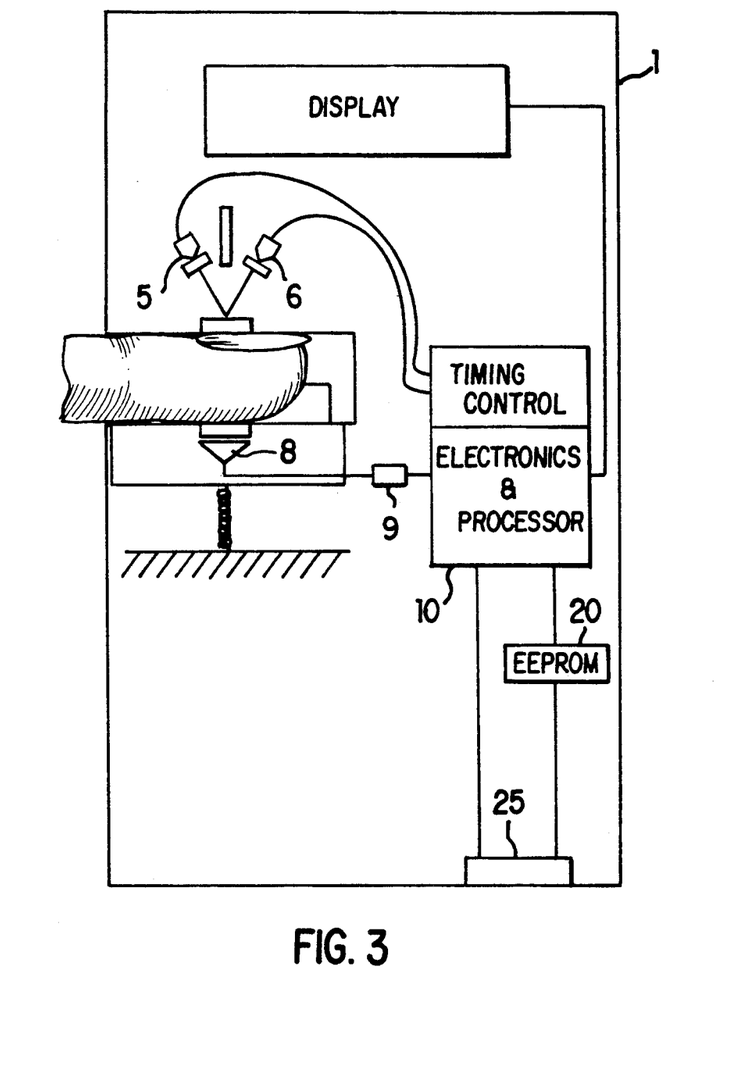
FIG. 3 is a front schematic view of a noninvasive near-infrared analysis instrument which can be generally calibrated according to the method of the present invention.

A near-infrared noninvasive blood glucose measurement instrument which can be generally calibrated employing the method of the present invention is illustrated schematically in FIG. 3. Noninvasive glucose meter 1 is designed to measure blood glucose levels through the distal portion of the test subject's finger. The analytical instrument contains at least one near-infrared energy source for introducing near-infrared energy into a test subject's finger. Near-infrared point sources 5 and 6 are shown for illustrative purposes in FIG. 3. The analytical instrument also utilizes detector 8 for detecting near-infrared energy emerging from the test subject's body part. Detector 8 is electrically connected to signal processing means 10 which, according to its programming, processes the signal produced by the detector 8 into a signal indicative of the quantity of glucose present in the blood of the test subject. Amplifier 9 amplifies the signal produced by the detector 8 before it is received into the processing means 10. Input/output connector 25 is electrically connected to the processing means 10 and allows the analytical instrument to be connected to a "host" instrument such as a computer. Input/output connector 25 enables the spectral clusters to be entered into the analysis instrument and stored in storage means 20, such as an electrically erasable programable read only memory (EEPROM). The noninvasive glucose meter 1 operates substantially as disclosed in application Ser. No. 07/565,302, incorporated herein by reference.

The general calibration method of the present invention is based upon the discovery that almost all individuals, independent of race, ethnic origin, medications, nail polish, and other parameters which distinguish one individual's near-infrared absorption measurements from another individual's measurements, can be categorized into approximately six different near-infrared spectral clusters. By comparing the test subject's individual near-infrared spectrum distribution to the spectral distribution curve of each different cluster, and using the calibration constants associated with the most closely matching cluster, accurate, general calibration can be accomplished for almost any individual.

Figure 4:
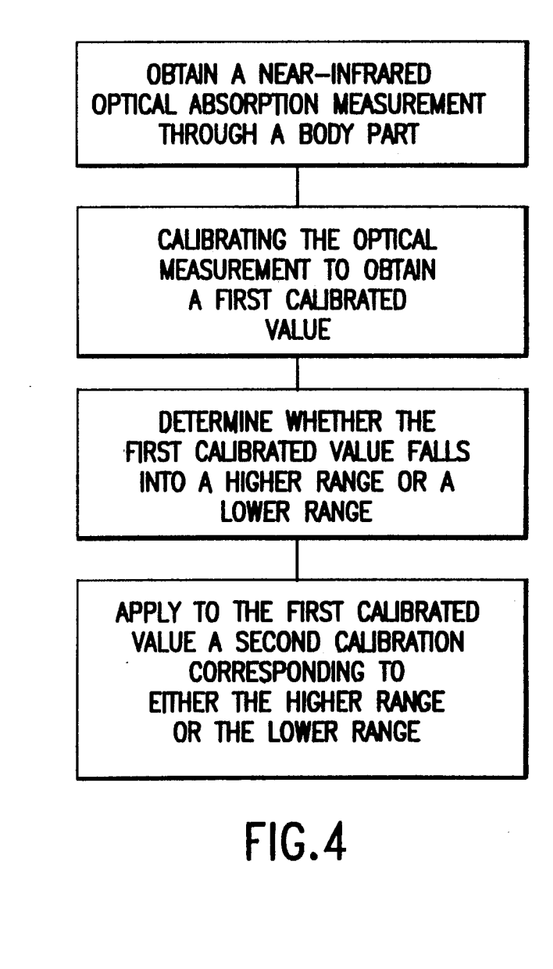
FIG. 4 is a flow diagram illustrating the method for calibrating a near-infrared analysis instrument for the measurement of blood glucose levels according to a second aspect of the present invention.

FIG. 4 illustrates a multiple calibration method according to another aspect of the present invention. The multiple calibration method effectively compensates for inaccuracies caused by large variations in measured constituent values. For example, in the blood glucose application there is typically a factor of twelve to one change in constituent value (i.e. 40 to 500 mg/dl). Stated differently, individual blood glucose concentrations can range anywhere from 40 to 500 mg/dl. Standard calibration approaches are linear techniques and are therefore normally limited to applications that have relatively small changes in a constituent value. Thus, large ranges in blood glucose constituent values are less amenable to linear analysis and can result in inaccurate calibration.

A similar problem exists in many agricultural applications. For example, the moisture level of corn, at the time of harvest, can be as high as 48%. However, after the corn is allowed to dry, the moisture level could be as low as 8%—a six to one variation of the constituent desired to be measured. The technique used in the agricultural application is to subdivide the calibration into two different ranges:

* Low Range—Calibration from 8% to 30%, and

* High Range—Calibration from 26% to 48%.

An individual operator selects either the low range calibration or the high range calibration. In using the above concept, the six to one range change is reduced to two ranges, with the maximum ratio of 3.8 to 1. These smaller ranges are more amenable to linear analysis, thereby, allowing accurate calibration.

Figure 5:
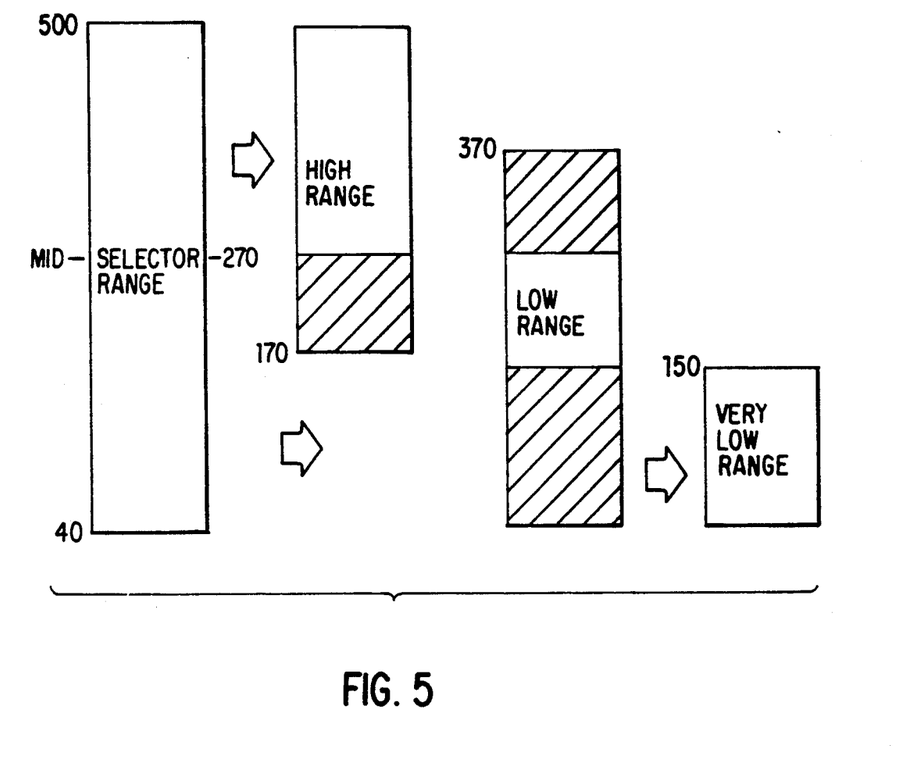
FIGS. 5 and 6 are block diagrams illustrating the method for calibrating a near-infrared analysis instrument.
Figure 6:
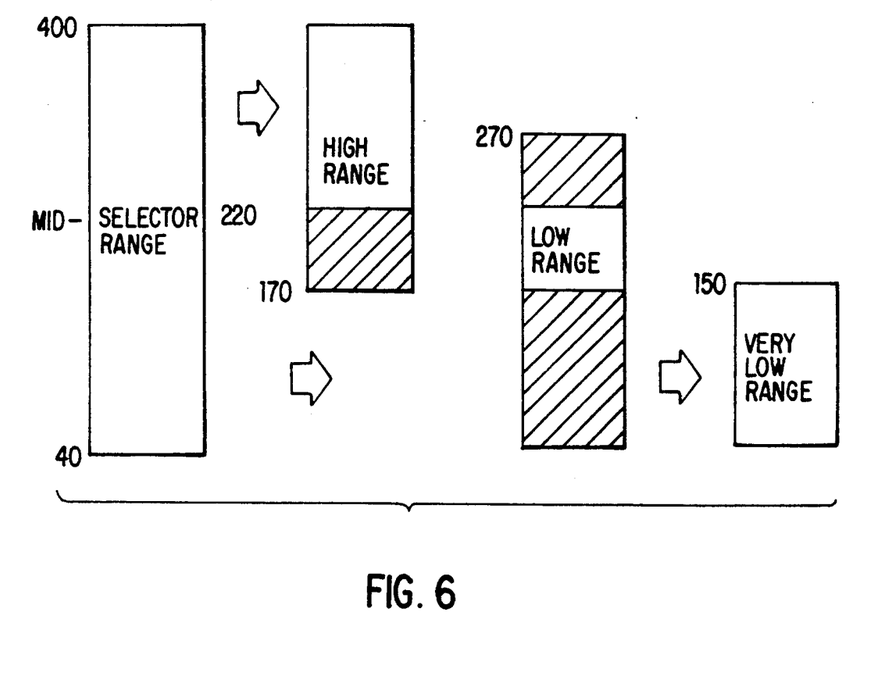

FIGS. 5 and 6 illustrate the multiple calibration concept applied to blood glucose analysis. An important advancement is that the present invention utilizes an initial calibration measurement which is provided to perform a calibration over the entire range of near-infrared data. The purpose of the initial calibration measurement is to decide which of the two alternate calibrations will be used—either the high range calibration or the lower range calibration.

As illustrated in FIG. 5, the initial calibration range is between 40 and 500 mg/dl. It is assumed that the initial calibration by the initial calibration measurement has a two sigma value (standard error of estimate) of 100 mg/dl. Thus, the high range extends up from 100 mg/dl below the midpoint of 270. Likewise, the low range extends downward from 100 mg/dl above the midpoint of 270.

Operation of the multiple calibration method will be described hereinafter. A person places her finger in the near-infrared blood glucose analysis instrument to obtain a near-infrared optical absorption measurement. The optical measurement is calibrated over substantially the entire range of possible blood analyte concentrations. This initial calibration will provide a first calibrated value, which is not displayed, that allows the instrument to select either the higher range or the lower range calibration. If it picks the high range calibration, the value obtained therefrom will be displayed. However, if it selects the low range calibration, and the result is less than approximately 150 mg/dl, then the instrument uses a more precise calibration for the range between approximately 40 and approximately 150 mg/dl.

FIG. 6 illustrates a similar example where the range is restricted to between 40 and 400 mg/dl.

Since a microprocessor utilized in the instrument is able to perform these types of calculations in milliseconds, the user never knows that these alternate calibrations are being selected. The actual glucose measurement value in displayed is a fraction of a second.

The multiple calibration method according to the present invention can be used to increase the accuracy of an individually custom calibrated near-infrared analysis instrument or an instrument utilizing the general calibration method as disclosed above. The multiple calibration method provides greater calibration accuracy used by itself or in combination with another calibration technique.

Although the invention has been described in connection with certain preferred embodiments, it is not limited to them. Modifications within the scope of the following claims will be apparent to those skilled in the art.

What is claimed is:

1. A method for calibrating a near-infrared analysis instrument for the measurement of a blood analyte, said method comprising:
    (a) obtaining a near-infrared optical absorption measurement through a body part of an individual;
    (b) comparing said optical absorption measurement with each spectral cluster of a plurality of spectral clusters, each of said spectral clusters having a set of calibration constants associated therewith;

(c) identifying which of said plurality of spectral clusters corresponds to said optical absorption measurement; and
(d) applying the set of calibration constants associated with the identified spectral cluster to said near-infrared optical absorption measurements to obtain a measurement of said blood analyte.

2. The method as set forth in claim 1, wherein said near-infrared optical measurement is made using energy of between about 600 to about 1000 nanometers.

3. The method as set forth in claim 1, wherein said plurality of spectral cluster is approximately six spectral clusters.

4. The method as set forth in claim 1, wherein said blood analyte is blood glucose levels.

* * * * *